US006372816B1

(12) United States Patent
Walz et al.

(10) Patent No.: US 6,372,816 B1
(45) Date of Patent: Apr. 16, 2002

(54) DENTAL MATERIALS PACKAGING AND METHOD OF USE

(75) Inventors: Uwe Walz; Kai P. Pflug, both of Constance; Ralf Wilner, Dienhausen; Markus Evers, Constance, all of (DE)

(73) Assignee: DENTSPLY DeTrey GmbH (DE)

( * ) Notice: Subject to any disclaimer, the term of this patent is extended or adjusted under 35 U.S.C. 154(b) by 0 days.

(21) Appl. No.: 09/498,004

(22) Filed: Feb. 4, 2000

Related U.S. Application Data (63) Continuation-in-part of application No. 09/340,096, filed on Jun. 25, 1999, now abandoned.

(51) Int. Cl.$^7$ ............................................. A61K 6/083

(52) U.S. Cl. ........................ 523/116; 526/281; 206/63.5

(58) Field of Search ............................. 523/116, 117, 523/118, 115; 526/281; 433/228.1; 206/63.5

(56) References Cited

U.S. PATENT DOCUMENTS

| | | | |
|---|---|---|---|
| 1,259,964 A | 3/1918 | Davis ......................... 206/528 |
| 2,305,642 A | 12/1942 | Sorenson ..................... 30/1.5 |
| 2,318,379 A | 5/1943 | Davis et al. ................ 206/63.3 |
| 2,486,321 A | 10/1949 | Sullivan ...................... 215/32 |
| 3,336,669 A | 8/1967 | Kramer ......................... 32/15 |
| 3,476,181 A | 11/1969 | Strauss et al. .............. 165/186 |
| 3,618,751 A | 11/1971 | Rich ............................ 206/47 |
| 3,651,932 A | 3/1972 | Mulhbauer ................... 206/47 |
| 3,655,037 A | 4/1972 | Lussier ....................... 206/635 |
| 3,756,386 A | 9/1973 | Marckkardt ................... 206/47 |
| 3,756,571 A | 9/1973 | Winberg ...................... 259/60 |
| 3,759,375 A | 9/1973 | Nappi ....................... 206/63.2 |
| 3,785,481 A | 1/1974 | Allet-Coche ................. 206/47 |
| 3,796,303 A | 3/1974 | Allet-Coche ................. 206/47 |
| 3,809,225 A | 5/1974 | Allet-Coche ................ 206/220 |
| 3,835,834 A | 9/1974 | Brown et al. .................. 128/2 |
| 3,907,106 A | 9/1975 | Purrmann et al. ........... 206/219 |
| 3,948,261 A | 4/1976 | Steiner ....................... 128/253 |
| 3,964,643 A | 6/1976 | Morane et al. ............. 222/145 |
| 4,081,077 A | 3/1978 | Franck ....................... 206/219 |
| 4,134,511 A | 1/1979 | Duessen ...................... 215/32 |
| 4,306,651 A | 12/1981 | Muhlbauer .................. 206/219 |
| 4,396,117 A | 8/1983 | Mulhbauer .................. 206/219 |
| D274,259 S | 6/1984 | Hamilton et al. ............. D24/16 |
| D275,517 S | 9/1984 | Hamilton et al. ............. D24/17 |
| 4,514,527 A | 4/1985 | Bowen ....................... 523/115 |
| 4,521,550 A | 6/1985 | Bowen ....................... 523/116 |
| 4,537,303 A | 8/1985 | Muhlbauer .................. 206/219 |
| 4,551,135 A | 11/1985 | Gorman et al. ................ 604/82 |
| D281,719 S | 12/1985 | Holewinski et al. ......... D24/16 |
| D281,813 S | 12/1985 | Holewinski et al. ......... D24/16 |
| 4,614,778 A * | 9/1986 | Kajiura et al. ............... 526/281 |
| 4,632,243 A | 12/1986 | Muhlbauer .................. 206/219 |
| D287,876 S | 1/1987 | Blatherwick et al. ........ D24/10 |
| 4,645,366 A | 2/1987 | Frohn ........................ 401/124 |
| 4,732,287 A | 3/1988 | Bennett ....................... 215/32 |
| 4,733,784 A | 3/1988 | Bennett ....................... 215/32 |
| 4,746,614 A | 5/1988 | Devaney, Jr. et al. ....... 435/295 |
| 4,765,984 A | 8/1988 | Vellekoop et al. ........... 424/441 |
| 4,767,326 A | 8/1988 | Bennett et al. ................ 433/90 |
| 4,786,534 A | 11/1988 | Aiken ....................... 428/34.2 |
| 4,838,851 A | 6/1989 | Shabo ........................... 604/1 |
| 4,880,111 A | 11/1989 | Bagwell et al. ........... 206/209.1 |
| 4,880,311 A | 11/1989 | Delebarre et al. ........... 366/101 |
| 4,889,228 A | 12/1989 | Gueret ........................ 206/209 |
| 4,900,315 A | 2/1990 | Lundqvist et al. ........... 604/311 |
| 4,952,204 A | 8/1990 | Korteweg ...................... 604/1 |
| 4,966,465 A | 10/1990 | Randklev .................... 366/111 |
| 4,973,248 A | 11/1990 | Sigler .......................... 433/90 |
| 4,995,519 A | 2/1991 | Rose et al. .................. 215/32 |
| 4,995,540 A | 2/1991 | Colin et al. ................. 222/132 |
| 5,001,803 A | 3/1991 | Discko, Jr. ................... 433/77 |
| 5,015,229 A | 5/1991 | Meyer et al. ................. 604/90 |
| 5,042,690 A | 8/1991 | O'Meara ...................... 222/83 |
| 5,064,306 A | 11/1991 | Gueret ........................ 401/133 |
| 5,074,414 A | 12/1991 | Romana ................... 206/362.4 |
| 5,087,677 A * | 2/1992 | Brekner et al. ............. 526/281 |
| 5,106,297 A | 4/1992 | Discko ......................... 433/77 |
| 5,109,979 A | 5/1992 | Cole .......................... 206/229 |
| 5,112,152 A | 5/1992 | McBride ..................... 401/132 |
| 5,112,227 A | 5/1992 | Bull .......................... 433/163 |
| 5,112,297 A | 5/1992 | Stalcup et al. ................ 604/1 |
| 5,131,845 A | 7/1992 | Feldman et al. ............. 433/104 |
| 5,169,315 A | 12/1992 | Bull .......................... 433/163 |
| 5,184,719 A | 2/1993 | Gordon .................... 206/209.1 |
| 5,197,496 A | 3/1993 | Nakamura .................. 132/200 |

(List continued on next page.)

FOREIGN PATENT DOCUMENTS

| | | |
|---|---|---|
| DE | 25 56 819 | 6/1977 |
| DE | 230828 | * 12/1985 |
| DE | 92 02 654.0 | 6/1992 |

(List continued on next page.)

OTHER PUBLICATIONS

TP Laboratories, Inc, Stright–Talk; vol. 15, No. 6, Oct. 1984.
TP Laboratories, Inc. The Package Makes It! E–Zetch Conditioning Capsules, 4 pages, 1994.
Ultradent Products, Inc.; Perma Quik Bonding System, 8 pages, 1994.
Kuraray Co., Ltd.; J. Morita USA Inc.; Clearfil Liner Bond 2; Light Cure Dental Adhsive System; 14 pages, 1995.
Kerr; OptBond™FL; 5 pages, 1996.
Clinical Characteristics Comparison; 1 page, May 1996.

*Primary Examiner*—Peter Szekely
(74) *Attorney, Agent, or Firm*—Dale R. Lovercheck; James B. Bieber (57) ABSTRACT

The invention provides a storage stable dental composition comprising a volatile organic solvent and a polymerizable material enclosed by a package, which includes a closure, such as a cover or plug and a container made of a copolymer of a cycloolefin and an open chain olefin. In accordance with an embodiment of the invention is provided a stored packaged dental product by the process including: enclosing a dental composition in a package with at least a substantial portion of an injection molded thermoplastic copolymer of a cycloolefin and an open chain olefin, and storing the dental composition in the package for at least 1 week.

37 Claims, 5 Drawing Sheets

U.S. PATENT DOCUMENTS

| | | | |
|---|---|---|---|
| 5,199,808 A | 4/1993 | Gueret | 401/133 |
| 5,213,860 A | 5/1993 | Laing | 428/36.92 |
| 5,240,415 A | 8/1993 | Haynie | 433/216 |
| 5,307,953 A | 5/1994 | Regan | 222/82 |
| 5,348,988 A | 9/1994 | Suh et al. | 523/118 |
| 5,525,647 A | 6/1996 | Eichmiller | 523/105 |
| 5,538,129 A | 7/1996 | Chester et al. | 206/63.5 |
| 5,609,581 A | 3/1997 | Fletcher et al. | 604/212 |
| 5,660,273 A | 8/1997 | Discko, Jr. | 206/229 |
| 5,695,340 A | 12/1997 | Lee et al. | 433/226 |
| 5,716,150 A | 2/1998 | Gueret | 401/129 |
| 5,732,862 A | 3/1998 | Bull | 224/217 |
| 5,819,921 A | 10/1998 | Schmid | 206/210 |
| 5,860,806 A | 1/1999 | Pranitis, Jr. et al. | 433/80 |
| 5,875,791 A | 3/1999 | Sheffler et al. | 132/218 |
| 5,947,622 A | 9/1999 | Akyildiz et al. | 401/129 |
| 6,033,143 A | 3/2000 | Gueret | 401/129 |
| 6,059,473 A | 5/2000 | Gueret | 401/129 |
| 6,059,570 A | 5/2000 | Dragan et al. | 433/80 |
| 6,082,999 A | 7/2000 | Tcherny et al. | 433/80 |
| 6,095,813 A | 8/2000 | Broyles | 433/80 |
| 6,099,307 A | 8/2000 | Discko, Jr. | 433/90 |

FOREIGN PATENT DOCUMENTS

| | | | |
|---|---|---|---|
| DE | 44 18 682 | 11/1995 | |
| DE | 196 48 820 | 5/1998 | |
| DE | 197 06 932 | 8/1998 | |
| DE | 197 22 765 | 12/1998 | |
| EP | 156 464 | 2/1985 | |
| EP | 582 355 | 2/1985 | |
| EP | 283 164 | 3/1988 | |
| EP | 407 870 | 4/1990 | |
| EP | 0 411 578 | 11/1994 | |
| GB | 842965 | 8/1960 | |
| GB | 1 527 544 | 10/1978 | |
| GB | 2 209 284 | 7/1988 | |
| JP | 275052 | * 12/1991 | 206/63.5 |
| WO | 96/03326 | 2/1996 | |
| WO | 98/23220 | 6/1998 | |

* cited by examiner

DENTAL MATERIALS PACKAGING AND METHOD OF USE

This is a continuation-in- part of U.S. patent application Ser. No. 09/340,096 filed Jun. 25, 1999 abandoned.

The invention relates to packaged dental compositions and methods of use thereof. The invention provides a storage stable packaged dental compositions having one or more volatile components and methods of use thereof. In accordance with the invention is provided a storage stable packaged dental compositions having one or more volatile components such a polar organic solvent and/or low molecular weight monomer.

One major problem with prior art injection molded packaging of dental compositions having one or more volatile components is the loss of a major portion of the volatile components from the dental compositions during storage. When the stored dental compositions with effectively reduced volatile components are used the originally available results are not provided. Thus, for example, dental adhesive and/or primer compositions stored in prior art injection molded packaging loose much, if not all, of their capacity for adhesion and/or priming. Other problems with prior art injection molded packaging of dental compositions include weight decrease of the polymeric material while enclosing the dental composition due to diffusion of components of the polymeric material from the polymeric material, and may cause contamination of the dental composition by components of the polymeric material. A weight increase of the polymeric material while enclosing the dental composition may be due to infusion of water from ambient humidity and/or solvent (or other components) from the polymeric material. Thus, a weight increase of the polymeric material may be indicative of a loss of solvent from the dental composition and/or water contamination of the dental composition. When the stored dental compositions (with effectively contaminated and/or depleted components) are used, the originally available results are not provided. These problems of prior art injection molded packaging of dental compositions are solved by the present invention.

BACKGROUND OF THE INVENTION

To ensure proper functioning of dental materials, they need to be protected from undergoing changes during storage. These changes of material may occur if external substances (e.g. moisture) penetrate the dental materials, or if parts of the dental materials (e.g. solvents) vanish. Therefore a suitable packaging is needed to prevent both intrusion of moisture into the dental materials and evaporation of solvent or other vital parts of the dental materials. Several ways of packaging have been tried, mostly using laminate materials consisting of different polymers. However, particularly for very small containers of dental materials (e.g. single unit dosage containers), laminate materials are not a viable solution as they are too difficult to shape and process.

It is an object of the invention to provide a storage stable dental composition comprising a volatile organic solvent and a polymerizable material enclosed by a package, which includes a closure such as a cover or plug, and a container comprising a copolymer of a cycloolefin and an open chain olefin.

It is an object of the invention to provide a storage stable dental composition comprising a volatile organic solvent and a polymerizable material enclosed by a package, which includes a notched container comprising a copolymer of a cycloolefin and an open chain olefin.

It is an object of the invention to provide a stored packaged dental product by the process including: enclosing a dental composition in a package with at least a substantial portion of an injection molded thermoplastic copolymer of a cycloolefin and an open chain olefin, and storing the dental composition in the package for at least 1 week.

It is an object of the invention to provide a stored packaged dental product by the process comprising: enclosing a dental composition including a volatile organic solvent in a package, at least a substantial portion of the package comprising thermoplastic polymer having a high chemical resistance and barrier capability toward polar organic solvents and water. After storing the dental composition in the package for at least two weeks at 37° C. at least 90 percent of the volatile organic solvent remains in the package.

As used herein open chain olefins are noncyclic olefins and include linear open chain olefins, straight chain olefins, branched chain olefins and branched open chain olefins. Open chain olefins are not closed chain olefins or ring olefins. Linear open chain olefins are most preferred open chain olefins for use in making copolymer for use in accordance with the invention.

As used herein volatile component refers to a component (of a dental composition) having vapor pressure more than that of water at 20° C.

As used herein volatile polar solvents refers to polar solvents, such as water, ethanol and acetone, which are at least as volatile as water at 20° C.

As used herein volatile organic solvents refers to organic solvents, such as ethanol and acetone, which are more volatile than water at 20° C.

As used herein moderately volatile organic solvent refers to an organic solvent, such as ethanol, which is more volatile than water, but not more volatile than ethanol i.e. vapor pressure more than that of water at 20° C., but less than or equal to 43 mm Hg at 20° C.

As used herein very volatile organic solvent refers to an organic solvent, such as acetone, which is more volatile than ethanol i.e. vapor pressure more than 43 mm Hg at 20° C.

As used herein high permeability barrier capability for water (and high water barrier capability) refers to polymeric material having a water vapor permeability below 0.07 g $(mm)(m^{-2})(d^{-1})$ measured by DIN 53122 at 23° C. and 85 percent relative humidity.

As used herein high penetration barrier capability for solvent of a polymeric material toward polar organic solvents refers to less than 2 percent by weight loss of polar organic solvents from a composition having at least 5 percent by weight of polar organic solvent(s) while enclosed in the polymeric material for at least two weeks at 37° C.

As used herein very high penetration barrier capability for solvent of a polymeric material toward polar organic solvents refers to less than 0.5 percent by weight loss of polar organic solvents from a composition having at least 5 percent by weight of polar organic solvent(s) while enclosed in the polymeric material for at least two weeks at 37° C.

As used herein high penetration barrier capability for water of a polymeric material toward water and humidity refers to a less than 3 percent by weight increase of a composition due to infusion of water through the polymeric material while the composition is enclosed in the polymeric material for at least two weeks at 37° C.

As used herein very high penetration barrier capability for water of a polymeric material toward water and humidity refers to a less than 1 percent by weight increase of a composition due to infusion of water through the polymeric material while the composition is enclosed in the polymeric material for at least two weeks at 37° C.

As used herein high chemical resistance of polymeric material refers to polymeric material having both a less than 3 percent by weight increase of the polymeric material, and a less than 0.5 percent by weight decrease of the polymeric material while the polymeric material is immersed in water and/or solvent for at least two weeks at 37° C. A weight decrease of the polymeric material while enclosing a dental composition (and/or immersed in water and/or solvent) may be due to diffusion of components of the polymeric material from the polymeric material, and may cause contamination of the dental composition by components of the polymeric material. A weight increase of the polymeric material while enclosing a dental composition and/or immersed in water and/or solvent may be due to infusion of water and/or solvent into the polymeric material, and may indicate that the polymeric material allows loss (or gain) of solvent from the dental composition and/or water contamination of a dental composition.

As used herein low molecular weight monomer refers to an acrylic monomer, such as methyl methacrylate having a gram molecular weight less than 150.

As used herein single unit dosage refers to volumes of a dental composition between 0.01 and 1 ml.

SUMMARY OF THE INVENTION

The invention provides a storage stable dental composition comprising a volatile organic solvent and a polymerizable material enclosed by a package, which includes a closure, such as a cover or plug, and a container. The container and plug are preferably made of a copolymer of a cycloolefin and an olefin. In a preferred embodiment of the invention, the container is notched. Preferably a thermoplastic polymeric packaging made of a copolymer of a cycloolefin and an open chain olefin is used. Copolymer of a cycloolefin and an olefin combines ease of processing by injection-molding with properties giving protection of the dental materials by high barrier capability and chemical resistance to water and polar organic solvents, such as acetone. Furthermore, containers made from copolymer of a cycloolefin and an olefin may be sealed by plugging with a plug or by thermal welding with a laminate plastic foil. The invention provides a stored packaged dental product by the process comprising: enclosing a dental composition in a package, at least a substantial portion of the package comprising thermoplastic polymer having a high barrier capability and chemical resistance to water and polar organic solvents. Preferably the thermoplastic polymer has high penetration barrier capability for solvent toward polar organic solvents and a high water barrier capability. After storing the dental composition in the package for at least two weeks at 37° C. at least 90 percent of the volatile organic solvent remains in the package.

The invention to provide a stored packaged dental product by the process including: enclosing a dental composition in a package with at least a substantial portion of an injection molded thermoplastic copolymer of a cycloolefin and an open chain olefin, and storing the dental composition in the package for at least 1 week.

DETAILED DESCRIPTION OF THE INVENTION

Figure 1:
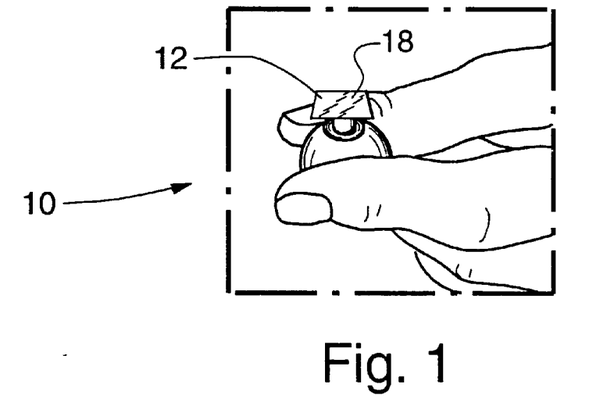
FIG. 1 is a perspective view of a covered container in a holder for use in accordance with the invention.
Figure 2:
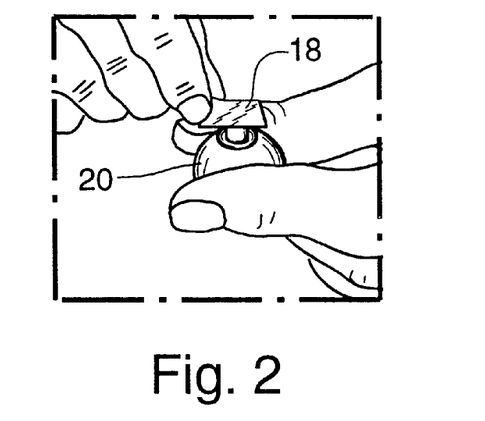
FIG. 2 is a perspective view of a container in a holder being uncovered for use in accordance with the invention.
Figure 3:
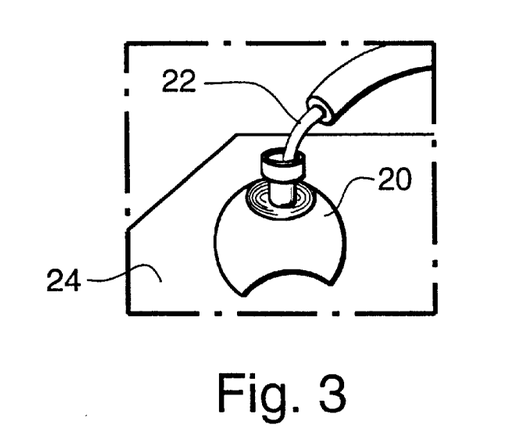
FIG. 3 is a perspective view of an uncovered container in a holder being used to dispense dental material in accordance with the invention.
Figure 4:
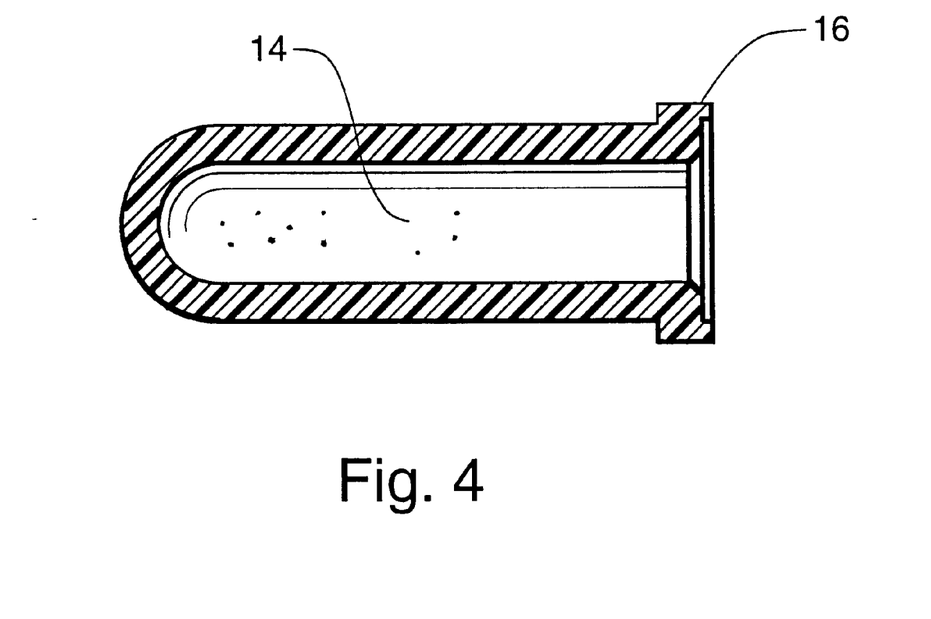
FIG. 4 is a cross-sectional side view of a container for use in accordance with the invention.
Figure 5:
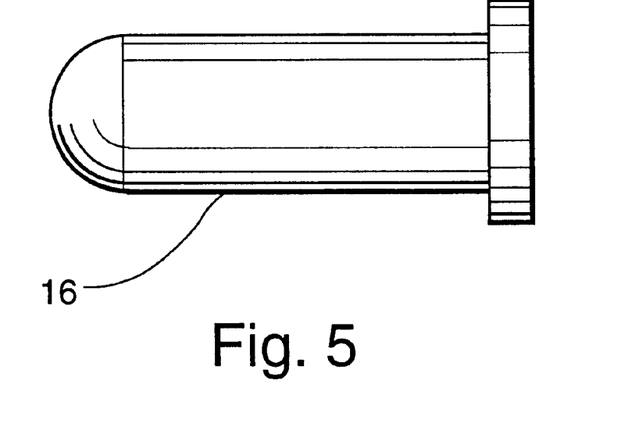
FIG. 5 is a side view of a container for use in accordance with the invention.

The invention is now described in reference to FIGS. 1 through 8. With more particular reference to FIGS. 1 through 5 is seen storage stable dental composition packaging system 10 having a package 12 and a volatile dental composition 14. The volatile dental composition 14 is enclosed by package 12. Package 12 includes container 16 and cover 18. Container 16 is made of a copolymer of a cycloolefin and an olefin. Dental composition 14 comprises a volatile organic solvent and a polymerizable material. The storage stable dental composition packaging system is stored for weeks, months or even years without significant loss of volatile organic solvent from dental composition 14 in closed package 12. In use container 16 is placed in holder 20 and uncovered for use by pealing cover 18 from container 16, as shown in FIG. 2. The user dispenses dental material by dipping applicator 22 into uncovered container 16, for example while container 16 is supported in a holder 20 supported on a horizontal surface 24, as shown in FIG. 3.

Figure 6:
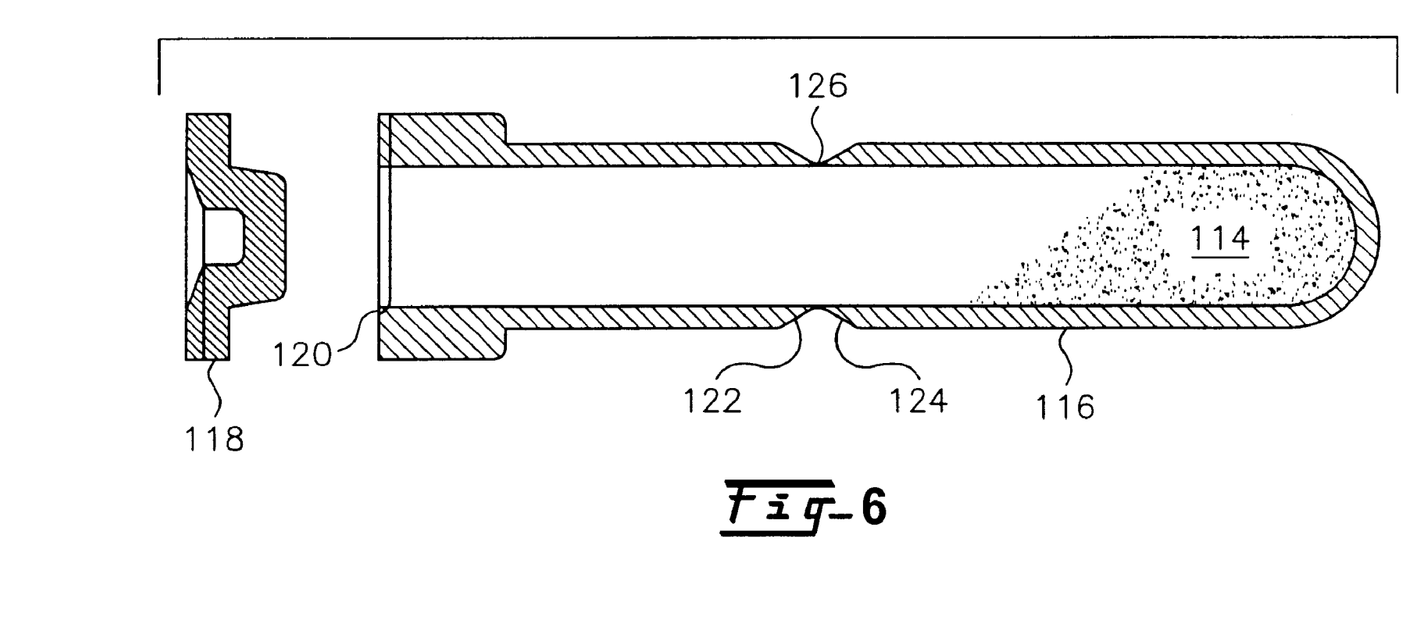
FIGS. 6 through 8 are cross-sectional side views of a notched container and plug for use as a package in accordance with the invention.
Figure 7:
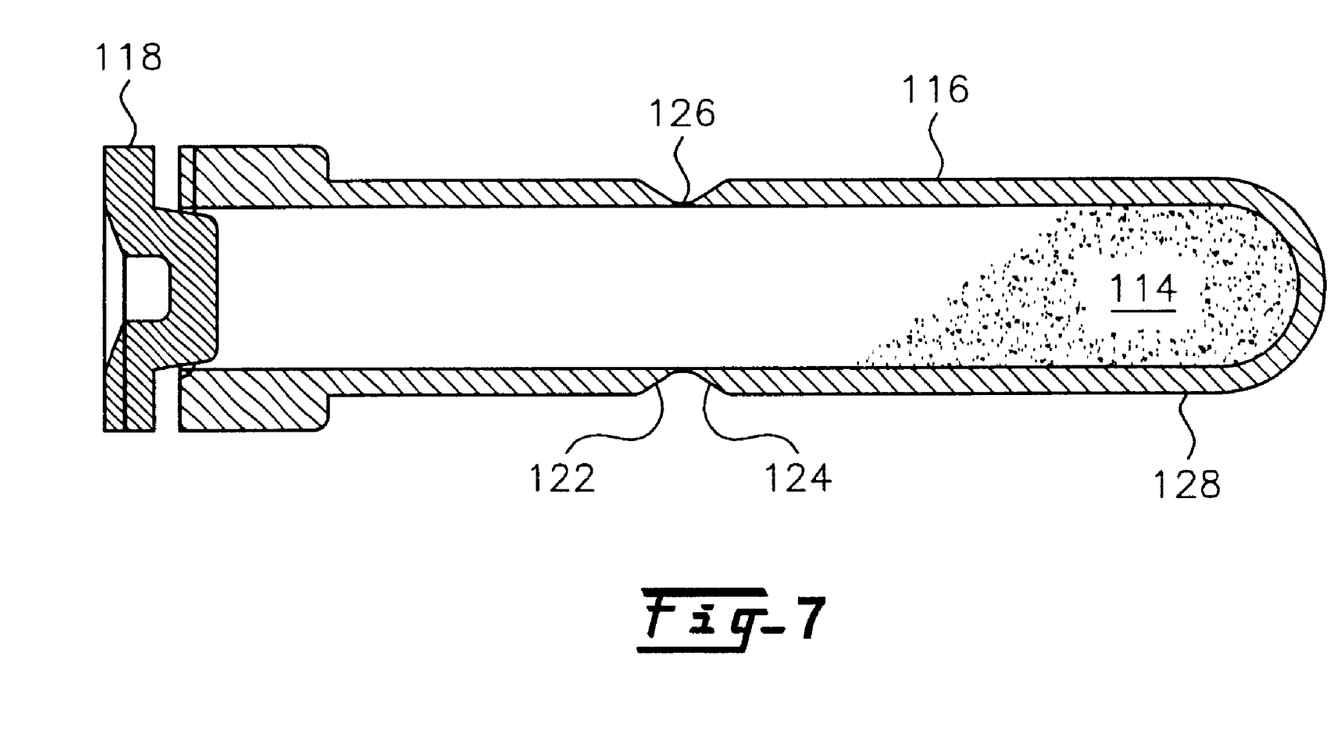
Figure 8:
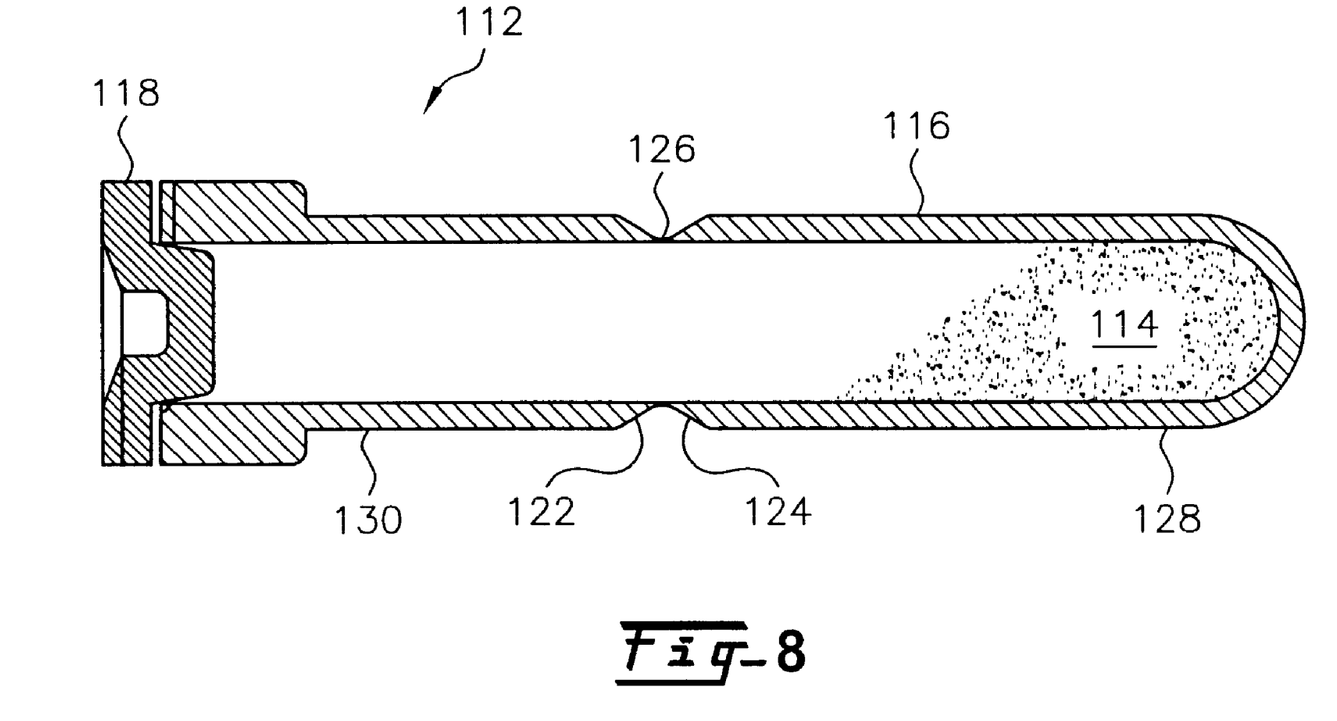

With more particular reference to FIGS. 6 through 8 is seen storage stable dental composition packaging system 110 having a plugged package 112 and a volatile dental composition 114. FIGS. 6 through 8 show the plugging progression with the plug shown prior to (FIG. 6) during (FIG. 7) and after (FIG. 8) plugging container 116. The volatile dental composition 114 is enclosed by plugged package 112. Plugged package 112 includes container 116 and plug 118. Container 116 has notch 126 formed by beveled faces 122 and 124. Notch 126 forms a groove which circumscribes container 116. Notch 126 marks the transition from base portion 128 of container 116 to top portion 130 of container 116. Container 116 is made of a copolymer of a cycloolefin and an olefin. Dental composition 114 comprises a volatile organic solvent and a polymerizable material. The storage stable dental composition packaging system is stored for weeks, months or even years without significant loss of volatile organic solvent from dental composition 114 in plugged package 112 For use, container 116 is preferably held vertically so that the volatile dental composition 114 is in the base portion 128, and base portion 128 is positioned below the top portion 130. Preferably plug 118 has a lacquer coating. Then container 116 is then broken at notch 126. The base portion 128 is placed in holder 20 for use. The top portion 130 and plug 118 are discarded. The user dispenses dental material by dipping applicator 22 into the base portion 128, for example while the base portion 128 is supported in holder 20 supported on a horizontal surface 24, in the same manner as the container shown In FIG. 3.

Exemplary thermoplastic polymeric cycloolefin- olefin-copolymer useful for storage stable packaging of dental composition in accordance with the invention are disclosed in EP 407,870; EP 156,464 and EP 283,164. Thus each discloses copolymers of cycloolefin and olefin useful for making containers and closures such as a covers and plugs, for use in accordance with the invention.

Copolymer of cycloolefin and open chain olefin useful for storage stable packaging of dental composition in accordance with the invention have the following properties: thermoplasticity, suitable for injection-molding, high moisture-barrier capability, high barrier capability towards organic solvents, high chemical resistance, high rigidity, and suitability for sealing with laminate foil via thermal welding or ultrasonic welding. Preferred copolymers of cycloolefin and open chain olefin for use in accordance with a preferred embodiment of the invention are copolymers of norbornene and ethylene for example the norbornene-ethylene-copolymer sold by Ticona GmbH as Topas 6013. Topas 6013 norbornene-ethylene-copolymer has the following properties: thermoplasticity, can be processed on conventional injection molding machines; high moisture vapour barrier: permeability of 0.035 $(g)(mm/m^2)(24\ hours)$ at 23° C., 85% relative humidity, high barrier capability towards polar organic solvents such as acetone, high resistance towards water, strong acids and bases, and polar organic solvents such as methanol, ethanol and acetone, high rigidity: yield stress of 66 MPa, tensile modulus of 3200 MPa and suitable for sealing with laminate foil via thermal welding.

In accordance with a preferred embodiment of the invention is provided a storage stable dental composition comprising a volatile organic solvent and a polymerizable material enclosed by a package, which includes a cover and a container comprising a copolymer of a cycloolefin and an olefin. Preferably the package has an open end sealed closed by a cover. Preferably the cover comprises a metal foil, a thermoplastic layer and a lacquer coating. Preferably the packaged dental composition is stored at about 23° C. for at least one year and at least 80 percent of the volatile organic solvent remains in the package. Preferably the storage stable packaged dental composition is stored at about 23° C. for at least two years and at least 90 percent of the volatile organic solvent remains in the package. Preferably the storage stable packaged dental composition is stored at about 23° C. for at least two years and at least 95 percent of the volatile organic solvent remains in the package. Preferably the volatile organic solvent of the storage stable packaged dental composition comprises acetone. Preferably the storage stable packaged dental composition is at least 20 percent by weight acetone both before and after storage at about 23° C. for two years and at least 95 percent of the volatile organic solvent remains in the package after the storage. Preferably the storage stable packaged dental composition is at least 20 percent by weight acetone both before and after storage at about 23° C. for one year and at least 90 percent of the acetone remains in the package after the storage. Preferably the storage stable packaged dental composition is at least 40 percent by weight acetone both before and after storage at about 23° C. for two years and at least 95 percent of the volatile organic solvent remains in the package after the storage. Preferably the storage stable packaged dental composition is at least 40 percent by weight acetone both before and after storage at about 23° C. for one year and at least 90 percent of the acetone remains in the package after the storage. Preferably the storage stable packaged dental composition is at least 50 percent by weight acetone both before and after storage at about 23° C. for two years and at least 95 percent of the volatile organic solvent remains in the package after the storage. Preferably the storage stable packaged dental composition is at least 50 percent by weight acetone both before and after storage at about 23° C. for one year and at least 90 percent of the acetone remains in the package after the storage.

In accordance with a preferred embodiment of the invention is provided a storage stable packaged dental composition wherein the dental composition comprising a solvent and a polymerizable material is enclosed by a container comprising a copolymer of a cycloolefin and an olefin, the dental composition, the packaged dental composition is at least 10 percent by weight solvent both before and after storage at about 43° C. for one week, and at least 99 percent of the solvent remains in the package after storage. Preferably at least 99.5 percent of the solvent remains in the package after storage. More preferably at least 99.8 percent of the solvent remains in the package after storage. Most preferably the solvent is a volatile organic solvent and at least 99.9 percent of the solvent remains in the package after storage.

In accordance with a preferred embodiment of the invention is provided a method of storing polymerizable material, comprising: providing a dental composition and a package, the package substantially enclosing the dental composition, the dental composition comprising a polar organic solvent at least a portion of the package comprising a thermoplastic polymer comprising a copolymer of a cycloolefin and an olefin and having a high penetration barrier capability for water and solvent and high chemical resistance, whereby when the dental composition is stored at about 23° C. in the package for at least two years and at least 90 percent of the polar organic solvent remains in the package. Preferably the dental composition, initially comprises at least 10 percent by weight of the solvent before storage at about 43° C. for one week and at least 99 percent of the solvent remains in the package after the storage. More preferably the dental composition, initially comprises at least 15 percent by weight of solvent before storage at about 43° C. for one week and at least 99.8 percent of the solvent remains in the package after storage.

In accordance with a preferred embodiment of the invention is provided a packed dental product, comprising: a package substantially enclosing a dental composition comprising a solvent. The package comprising a container and a plug. The container and plug each are molded from a thermoplastic copolymer of a cycloolefin and an olefin and having a high permeability barrier capability for water and high chemical resistance. When the dental composition is stored at about 23° C. in the package for at least two years and at least 99 percent of the dental composition remains in the package. Preferably the container and the plug are injection molded. Preferably the package has a longest dimension less than 4 cm. Preferably the container has a longest dimension less than 2 cm. Preferably the container and the plug each comprises a thermoplastic copolymer of a cycloolefin and an open chain olefin having a high permeability barrier capability for water and high chemical resistance towards both water and the solvent. Preferably the copolymer has a permeability to water of less than 0.07 $(g)(mm/m^2)(24\ hours)$ at 23° C. and 85% relative humidity. More preferably the copolymer has a permeability to water of less than 0.05 $(g)(mm/m^2)(24\ hours)$ at 23° C. and 85% relative humidity.

In accordance with a preferred embodiment of the invention is provided a packed dental product, comprising: a package substantially enclosing a dental composition comprising a solvent. The package comprising a container and a cover. At least a portion of the container comprises a thermoplastic copolymer of a cycloolefin and an olefin and having a high permeability barrier capability for water and high chemical resistance. The cover comprises a metal foil. When the dental composition is stored at about 23° C. in the package for at least two years and at least 99 percent of the dental composition remains in the package. Preferably the cover comprises a polymeric film, such as A polyethylene or polypropylene laminated to the metal foil. Preferably the cover comprises a molded member, sheet, film or coating of thermoplastic polymer comprising a copolymer of a cycloolefin and an olefin and having a high permeability barrier capability for water and high chemical resistance. Preferably the container is injection molded. Preferably the package has a longest dimension less than 4 cm. Preferably the container has a longest dimension less than 2 cm. Preferably the cover comprises a thermoplastic polymer comprising a copolymer of a cycloolefin and an open chain olefin and having a high permeability barrier capability for water and high chemical resistance towards both water and the solvent. Preferably the copolymer has a permeability to water of less than 0.07 (g) (mm/m$^2$)(24 hours) at 23° C. and 85% relative humidity. More preferably the copolymer has a permeability to water of less than 0.05 (g)(mm/m$^2$)(24 hours) at 23° C. and 85% relative humidity.

In accordance with a preferred embodiment of the invention is provided a stored packaged dental product by the process comprising: enclosing a dental composition in a package, at least a substantial portion of the package comprising thermoplastic polymer having a high resistance toward polar organic solvents and a high water barrier capability, and storing the dental composition in the package for at least two weeks at 37° C. and after the two weeks at least 90 percent of the volatile organic solvent remains in the package. Preferably the package includes a molded portion and a laminated portion. Preferably the package is made by sealing a molded portion to a laminated portion. Preferably the thermoplastic polymer of the molded portion is injection molded and has an average thickness from about 0.4 mm to about 6 mm. More preferably the injection molded thermoplastic polymer has an average thickness from about 0.6 mm to about 4 mm. Most preferably the injection molded thermoplastic polymer has an average thickness from about 0.8 mm to about 3 mm. Preferably the thermoplastic polymer is a copolymer of a cycloolefin and an open chain olefin. The open chain olefin is preferably a straight open chain olefin or a branched open chain olefin. The open chain olefin of the copolymer used to mold at least a portion of the package, preferably has a gram molecular weight which is less than half of the gram molecular weight of the cycloolefin of the copolymer. Preferably the package has a cover over a readily opened end, and the cover comprises a polymeric film, such as polyethylene or polypropylene laminated to the metal foil such as aluminum foil.

In accordance with a preferred embodiment of the invention is provided a dental method of use, of a thermoplastic polymer, having a high permeability barrier capability for water, high chemical resistance, as at least a substantial portion of a package enclosing a dental composition comprising at least 3 percent by weight of volatile organic solvent, whereby the dental composition is stored in the package at about 23° C. for at least two years and after the two years at least 90 percent of the volatile organic solvent remains in the package. Preferably the dental composition comprises at least 5 percent by weight of volatile organic solvent. More preferably the dental composition comprising at least 10 percent by weight of volatile organic solvent.

Comparative Example 1

A single unit dose rocket shaped package as disclosed in U.S. Pat. No. 5,860,806 (The Kerr corporation) was used as packaging to enclose 132 mg of acetone-based dental adhesive. This enclosed adhesive initially contained 66.12% acetone and 33.88% non-volatile components. After 1 month storage of the adhesive at 50° C. in the single unit dose rocket shaped package, evaporation of 85.4 mg +or −4.6 mg was measured, equaling a weight loss of 65%, indicating almost complete loss of all volatile solvent.

Comparative Example 1 clearly shows that the single unit dose packaging shaped package is not suitable for storing the adhesive, as the packaging does not have a sufficient barrier capability for the solvent. In contrast, as described in Example 2, an acetone-based dental adhesive was stable without significant solvent vaporization at elevated temperatures in the packaging described in this invention.

The following examples are given to show the suitability of copolymers of cycloolefin and open chain olefin as packaging materials for dental materials.

EXAMPLE 1

A small container having the shape shown in FIG. 1 was molded by injection molding with a wall thickness of about 1 mm from norbomene-ethylene-copolymer, sold by Ticona GmbH as Topas 6013. The container was filled with approximately 175µl acetone and sealed by thermal welding with a laminate foil (KV 611-TD 131-0022, supplier: Lawson Mardon Singen, three layers: 12 µm PET|12 µm Al|50 µm LDPE) to form a storage stable packaged dental composition. The packaged dental composition was then weighed and stored at elevated temperature. After 1 month at 43° C., the packaged dental composition was weighed again. No significant weight change was detected.

Because there was no significant weight change, there was no significant acetone loss after 1 month at 43° C. which shows that the package has a high barrier capability for acetone.

Less than 2 percent by weight of dental composition was lost when stored in packaging of EXAMPLE 1 for one month at about 43° C. Thus, the packaging of EXAMPLE 1 is far superior to prior art packaging (see Comparative Example 1) in preventing loss of weight of volatile polar solvent from dental compositions enclosed therein.

EXAMPLE 2

Three small containers each having the shape shown in FIG. 1 were molded with a wall thickness of about 1 mm from norbomene-ethylene-copolymer, sold by Ticona GmbH as Topas 6013 by injection molding. The container was filled with approximately 175 µl acetone-based dental adhesive (12.05 grams 2,7,7,9,15-pentamethyl-4,13-dioxo-3,14-dioxa 5,12-diaza-hexadecane-1,16-diyl-dimethacrylate (urethane dimethacrylate: UDMA); 7.44 grams dipentaerythritol pentacrylate phosphoric acid ester (PENTA); 0.30 grams 2,6-di-tert-butyl-4-methyl phenol (BHT); 0.30 grams camphorquinone; 0.89 grams 4-ethyldimethylaminobenzoate (EDAB); 0.30 grams cetylamine hydrofluoride; 66.14 grams acetone; 3.46 grams 7,7,9,63,63,65 hexamethyl-4,13,60,69-tetra-oxo-3,14,19,24,29,34,39,44, 49, 54,59,70-dodecanaoxa-5,12,61,68-tetraazadoheptacotane-1,72 diyl-dimethacrylate (urethane dimethacrylate resin R5-62-1); 2.06 grams trimethylolpropane trimethacrylate (TMPTMA); 4.41 grams diethyleneglycol dimethacrylate (DEGMA); and 2.65 grams of SiO$_2$ having an average particle size of about 10 nm. Then the container was sealed by thermal welding with a laminate foil (KV 611-TD 131-0022, supplier: Lawson Mardon Singen, three layers: 12 µm PET|12 µm Al|50 µm LDPE) to form storage stable packaged dental compositions. Then the packaged dental compositions were each weighed and stored at 23° C., 37° C. or 43° C. for one month. After 1 month at 23° C., 37° C. and 43° C., the packaged dental compositions were weighed again. The weight change detected between the weight of the package before and after storage was −0.56 percent after 1 month at 23° C.; −1.64 percent after 1 month at 37° C.; and −1.95 percent after 1 month at 43° C.

Because there was no significant weight change, there was no significant acetone loss after 1 month at 23° C., 37° C. and 43° C., which shows that each package has a high penetration barrier capability for solvent for acetone.

EXAMPLE 3

Three small containers each having the shape shown in FIG. 1 were molded with a wall thickness of about 1 mm from norbornene-ethylene-copolymer, sold by Ticona GmbH as Topas 6013 by injection molding. The container was filled with approximately 175 μl acetone-based dental adhesive (12.05 grams 2,7,7,9,15-pentamethyl-4,13-dioxo-3,14-dioxa 5,12-diaza-hexadecane-1,16-diyl-dimethacrylate (urethane dimethacrylate: UDMA); 7.44 grams dipentaerythritol pentacrylate phosphoric acid ester (PENTA); 0.30 grams 2,6-di-tert-butyl-4-methyl phenol (BHT); 0.30 grams camphorquinone; 0.89 grams 4-ethyldimethylaminobenzoate (EDAB); 0.30 grams cetylamine hydrofluoride; 66.14 grams acetone; 3.46 grams 7,7,9,63,63,65 hexamethyl-4,13,60,69-tetra-oxo-3,14,19,24,29,34,39,44, 49, 54,59,70-dodecanaoxa-5,12,61,68-tetra-azadoheptacotane-1,72 diyl-dimethacrylate (urethane dimethacrylate resin R5-62-1); 2.06 grams trimethylolpropane trimethacrylate (TMPTMA); 4.41 grams diethyleneglycol dimethacrylate (DEGMA); and 2.65 grams of $SiO_2$ having an average particle size of about 10 nm. Then the container was sealed by thermal welding with a laminate foil (KV 611-TD 131-0022, supplier: Lawson Mardon Singen, three layers: 12 μm PET|12 μm Al|50 μm LDPE) to form storage stable packaged dental compositions. Then the packaged dental compositions were each weighed and stored at 37° C. for two weeks. After 2 weeks at 37° C., the packaged dental compositions were weighed again. No significant weight change was detected. The containers were then opened and adhesive properties of the acetone-based dental adhesive were tested by using the adhesive in a shear bond strength test. The values obtained (with NRC pretreatment, one coat of the adhesive, restorative material Spectrum TPH) were 26.7 MPa±3.5 MPa to dentin (before storage: 24.9±4.5 MPa) and 23.1±4.6 MPa to enamel (before storage: 20.5±3.9 MPa). This shows that the adhesive properties of the adhesive were not adversely affected by the storage in the sealed containers at elevated temperature.

EXAMPLE 4

A small container and a plug having the shapes shown in FIG. 6 are molded by injection molding with a wall thickness of about 1 mm from norbomene-ethylene-copolymer, sold by Ticona GmbH as Topas 6013. The container was filled with approximately 175 μl acetone and then plugged with the plug to form a storage stable dental composition packaged in a plugged container as shown in FIG. 8. The packaged dental composition is then weighed and stored at elevated temperature. After 1 month at 43° C., the packaged dental composition is weighed again. No significant weight change is detected.

Because there is no significant weight change, there is no significant acetone loss after 1 month at 43° C. which shows that the package has a high barrier capability for acetone.

Less than 2 percent by weight of dental composition is lost when stored in packaging of EXAMPLE 4 for one month at about 43° C. Thus, the packaging of EXAMPLE 4 is far superior to prior art packaging (see Comparative Example 1) in preventing loss of weight of volatile polar solvent from dental compositions enclosed therein.

EXAMPLE 5

The storage stable packaged dental composition shown in FIG. 8 and formed and stored as decribed in Example 4 is held by the user with the central container axis positioned in a vertically and with base portion (128) of container (116) between the thumb and forefinger of one hand and plugged top portion (130) of container (116) between the thumb and forefinger of the other hand. Dental composition (114) which comprises a volatile organic solvent and a polymerizable material flows into base portion (128) of container (116). The user bends the container (116) which breaks at the notch (126) which forms a groove which circumscribes container (116). The user discards plugged top portion (130) of container (116). The user places the base portion (128) of container (116) which contains the dental composition (114) in a holder supported on a horizontal surface to support it in the same manner as container (16) is supported in holder (20) which is supported on a horizontal surface (24), as shown in FIG. 3. The user then dips an applicator brush through the broken end of the base portion (128) of container (116) into the dental composition (114) and then lifts the applicator brush with a portion of the dental composition (114) out of the the base portion (128) of container (116). The user then uses the applicator brush to apply the dental composition (114) to a tooth in a patient's mouth.

Various alterations and modifications of the invention will be apparent to those of ordinary skill in the art without departing from the scope and spirit of this invention. Accordingly, it should be understood that the invention is not limited to the illustrative embodiments set forth herein.

What is claimed is:

1. A storage stable packaged dental composition, comprising:

a package and a dental composition, said dental composition being enclosed by said package, said package comprising a container, said container comprising a copolymer of a cycloolefin and an open chain olefin, said container having a wall with an average thickness from about 0.4 mm to about 6 mm, said dental composition, comprising a polymerizable material, and at least 10 percent by weight of volatile organic solvent, and at least 99 percent of said solvent remains in said dental composition in said container after storage at about 43° C. for one week.

2. The storage stable packaged dental composition of claim 1 wherein said package further comprises a closure.

3. The storage stable packaged dental composition of claim 2 wherein said closure comprises a metal foil.

4. The storage stable packaged dental composition of claim 2 wherein said closure comprises a thermoplastic layer.

5. The storage stable packaged dental composition of claim 2 wherein said closure comprises a lacquer coating.

6. The storage stable packaged dental composition of claim 1 wherein said packaged dental composition is stored at about 23° C. for at least one year and at least 80 percent of said volatile organic solvent remains in said package.

7. The storage stable packaged dental composition of claim 1 wherein said packaged dental composition is stored at about 23° C. for at least two years and at least 90 percent of said volatile organic solvent remains in said package.

8. The storage stable packaged dental composition of claim 1 wherein said packaged dental composition is stored at about 23° C. for at least two years and at least 95 percent of said volatile organic solvent remains in said package.

9. The storage stable packaged dental composition of claim 1 wherein said volatile organic solvent comprises acetone.

10. The storage stable packaged dental composition of claim 1 wherein said packaged dental composition is at least 20 percent by weight acetone both before and after storage at about 23° C. for two years and at least 95 percent of said volatile organic solvent remains in said package after said storage.

11. The storage stable packaged dental composition of claim 1 wherein said packaged dental composition is at least 20 percent by weight acetone both before and after storage at about 23° C. for one year and at least 90 percent of said acetone remains in said package after said storage.

12. The storage stable packaged dental composition of claim 1 wherein said packaged dental composition is at least 40 percent by weight acetone both before and after storage at about 23° C. for two years and at least 95 percent of said volatile organic solvent remains in said package after said storage.

13. The storage stable packaged dental composition of claim 1 wherein said packaged dental composition is at least 40 percent by weight acetone both before and after storage at about 23° C. for one year and at least 90 percent of said acetone remains in said package after said storage.

14. The storage stable packaged dental composition of claim 1 wherein said packaged dental composition is at least 50 percent by weight acetone both before and after storage at about 23° C. for two years and at least 95 percent of said volatile organic solvent remains in said package after said storage.

15. The storage stable packaged dental composition of claim 1 wherein said packaged dental composition is at least 50 percent by weight acetone both before and after storage at about 23° C. for one year and at least 90 percent of said acetone remains in said package after said storage.

16. A storage stable packaged dental composition, comprising:
a package and a dental composition,
said dental composition being enclosed by said package,
said package comprising a container, said container comprising a copolymer of a cycloolefin and an open chain olefin,
said dental composition, comprising a volatile solvent and a polymerizable material,
said packaged dental composition being at least 10 percent by weight solvent, before storage at about 43° C. for one week and at least 99 percent of said solvent remains in said dental composition in said package after said storage.

17. The storage stable packaged dental composition of claim 16 wherein said volatile solvent comprises acetone and at least 99.5 percent of said solvent remains in said package after said storage.

18. The storage stable packaged dental composition of claim 16 wherein at least 99.8 percent of said solvent remains in said package after said storage.

19. The storage stable packaged dental composition of claim 16 wherein said solvent is a volatile organic solvent and at least 99.9 percent of said solvent remains in said package after said storage.

20. A packed dental product, comprising:
a dental composition and
a package, said package comprising a container and a closure, said package substantially enclosing said dental composition, said dental composition comprising a volatile solvent, at least a portion of said container comprising a thermoplastic polymer comprising a copolymer of a cycloolefin and an open chain olefin and having a high permeability barrier capability for water and high chemical resistance,
whereby when said dental composition is stored at about 23° C. in said package for at least two years and at least 99 percent of said volatile solvent remains in said dental composition in said package.

21. The product of claim 20 wherein said closure comprises a molded polymeric material or a polymeric film laminated to a foil.

22. The product of claim 20 wherein said container comprises injection molded polymeric material, said container has a notch and said container is readily broken at said notch, and said closure comprises injection molded polymeric material.

23. The product of claim 20 wherein said package has a longest dimension less than 4 cm.

24. The product of claim 20 wherein said container has a longest dimension less than 2 cm.

25. The product of claim 20 wherein said volatile solvent comprises acetone.

26. The product of claim 20 wherein said cover comprises a metal foil.

27. The product of claim 20 wherein said cover closure comprises a thermoplastic polymer comprising a copolymer of a cycloolefin and an olefin and having a high permeability barrier capability for water and high chemical resistance.

28. The product of claim 20 wherein said copolymer has a permeability to water of less than 0.07 $(g)(mm/m^2)(24$ hours) at 23° C. and 85% relative humidity.

29. The product of claim 20 wherein said copolymer has a permeability to water of less than 0.05 $(g)(mm/m^2)(24$ hours) at 23° C. and 85% relative humidity.

30. A stored packaged dental product by the process comprising:
enclosing a dental composition having at least one volatile component in a package, at least a substantial portion of said package comprising thermoplastic polymer having a high chemical resistance and a high permeability barrier capability for water, and
storing said dental composition in said package for at least two weeks at 37° C. and after said two weeks at least 90 percent of said volatile component remains in said dental composition in said package.

31. A stored packaged dental product by the process comprising:
enclosing a dental adhesive composition comprising volatile solvent in a package, at least a substantial portion of said package comprising an injection molded thermoplastic copolymer of a cycloolefin and an open chain olefin, and effectively retaining said volatile solvent in said dental composition while storing said dental composition in said package for at least 1 week at about 23° C.

32. The product of claim 29 wherein said dental composition is a single unit dosage and said thermoplastic polymer has a high chemical resistance, a high penetration barrier capability for water, high penetration barrier capability for solvent and a high permeability barrier capability for water.

33. The stored packaged dental product of claim 31 wherein
said solvent comprises a polar organic solvent, said copolymer of a cycloolefin and an open chain olefin has a high permeability barrier capability for water and high chemical resistance, and at least 90 percent of said polar organic solvent remains in said dental composition In said package while stored at about 23° C. for about two years.

34. The stored packaged dental product by the process of claim 31 wherein said dental composition comprises at least 10 percent by weight of said solvent, and at least 99 percent of said solvent remains in said dental composition in said package, after said storage.

35. The stored packaged dental product by the process of claim 31 wherein said dental composition comprises at least 15 percent by weight of said solvent, and at least 99.8 percent of said solvent remains in said dental composition in said package, after said storage.

36. The stored packaged dental product by the process of claim 30 wherein after said storing said dental composition bonds to dentin with a bond strength at least as high as said dental composition bonds to dentin before said storing.

37. The stored packaged dental product by the process of claim 31 wherein said dental composition bonds to dentin with effectively the same amount of bond strength before and after said storing.

* * * * *